(12) United States Patent
Van Beek et al.

(10) Patent No.: US 10,638,989 B2
(45) Date of Patent: May 5, 2020

(54) METHOD AND DEVICE FOR CONTROLLING MOVEMENT OF A MOTORIZED C-ARM

(71) Applicant: SURGIVISIO, La Tronche (FR)

(72) Inventors: Laurence Van Beek, Saint Martin d'Uriage (FR); David Armand, Saint Egreve (FR); Arnaud Pierre, La Tronche (FR); Stephane Lavallee, St. Martin d'Uriage (FR); Markus Fleute, Volgelsheim (FR)

(73) Assignee: SURGIVISIO, La Tronche (FR)

( * ) Notice: Subject to any disclaimer, the term of this patent is extended or adjusted under 35 U.S.C. 154(b) by 164 days.

(21) Appl. No.: 15/765,995

(22) PCT Filed: Oct. 6, 2016

(86) PCT No.: PCT/EP2016/073925
§ 371 (c)(1),
(2) Date: Apr. 4, 2018

(87) PCT Pub. No.: WO2017/060383
PCT Pub. Date: Apr. 13, 2017

(65) Prior Publication Data
US 2018/0289346 A1    Oct. 11, 2018

(30) Foreign Application Priority Data
Oct. 6, 2015  (FR) ..................... 15 18855

(51) Int. Cl.
*A61B 6/00* (2006.01)

(52) U.S. Cl.
CPC ............ *A61B 6/4441* (2013.01); *A61B 6/465* (2013.01); *A61B 6/467* (2013.01); *A61B 6/4405* (2013.01); *A61B 6/547* (2013.01)

(58) Field of Classification Search
CPC ....... A61B 6/4441; A61B 6/467; A61B 6/465; A61B 6/547; A61B 6/4405
(Continued)

(56) References Cited

U.S. PATENT DOCUMENTS 5,155,757 A * 10/1992 Sakaniwa ............ A61B 6/4464
378/196
6,348,911 B1 * 2/2002 Rosenberg ............ A63F 13/285
345/161
(Continued)

FOREIGN PATENT DOCUMENTS

DE  102013219145 A1   4/2015
JP  2010-035939 A     2/2010

OTHER PUBLICATIONS

International Search Report and Written Opinion received for PCT Patent Application No. PCT/EP2016/073925, dated Jan. 16, 2017, 10 pages.
(Continued)

*Primary Examiner* — David P Porta
*Assistant Examiner* — Gisselle M Gutierrez
(74) *Attorney, Agent, or Firm* — Womble Bond Dickinson (US) LLP

(57) ABSTRACT

The invention relates to a method for controlling movement of a motorized C-arm, comprising:
receiving position information of a user (U) relative to the C-arm (1),
continuously receiving current position information of the C-arm (1) relative to a reference position of the C-arm,
from said current position information and from the position information of the user, computing a graphical representation of the current position of the C-arm according to the user's point of view,
from the computed graphical representation of the current position of the C-arm, computing a graphical represen-
(Continued)

tation of at least one command button suited to the current position information of the C-arm and to the user's point of view to move the C-arm in a determined direction according to a respective degree of freedom, displaying on a control panel a graphical user interface (7) comprising said computed representation (70) of the current position of the C-arm and said at least one command button (710).

14 Claims, 11 Drawing Sheets

(58) Field of Classification Search
USPC .......................................................... 378/197
See application file for complete search history.

(56) References Cited

U.S. PATENT DOCUMENTS

| | | | | |
|---|---|---|---|---|
| 8,641,663 | B2* | 2/2014 | Kirschenman | A61B 17/2909 |
| | | | | 604/95.01 |
| 9,492,131 | B2* | 11/2016 | Meek | A61B 6/4476 |
| 9,642,584 | B2* | 5/2017 | Niebler | A61B 6/4441 |
| 2002/0131554 | A1* | 9/2002 | Fleming | A61L 2/0041 |
| | | | | 378/119 |
| 2002/0131555 | A1* | 9/2002 | Fleming | A61L 2/082 |
| | | | | 378/119 |
| 2003/0068011 | A1* | 4/2003 | Johnson | A61B 5/7475 |
| | | | | 378/115 |
| 2004/0127789 | A1* | 7/2004 | Ogawa | A61B 6/481 |
| | | | | 600/425 |
| 2005/0004802 | A1* | 1/2005 | Johnson | A61B 5/7475 |
| | | | | 704/275 |
| 2013/0088452 | A1* | 4/2013 | Glaser-Seidnitzer | ........................ |
| | | | | G06F 3/0488 |
| | | | | 345/173 |
| 2013/0230142 | A1* | 9/2013 | Murata | A61B 6/4405 |
| | | | | 378/62 |
| 2013/0243160 | A1 | 9/2013 | Graumann et al. | |
| 2015/0085986 | A1* | 3/2015 | Dinse | A61B 6/10 |
| | | | | 378/98 |
| 2015/0216489 | A1* | 8/2015 | Everaerts | A61B 6/12 |
| | | | | 600/424 |
| 2016/0074000 | A1* | 3/2016 | Uehara | A61B 6/4405 |
| | | | | 378/69 |
| 2018/0074595 | A1* | 3/2018 | Isaacs | A61B 6/486 |

OTHER PUBLICATIONS

International Preliminary Report on Patentability received for PCT Patent Application No. PCT/EP2016/073925, dated Apr. 19, 2018, 8 pages.

European Search Report and Written Opinion received for EP Patent Application No. 15188553.0, completed on Mar. 31, 2016, 8 pages.

* cited by examiner

METHOD AND DEVICE FOR CONTROLLING MOVEMENT OF A MOTORIZED C-ARM

FIELD OF THE INVENTION

The invention relates to a method and a device for controlling movement of a motorized C-arm by a user in an operating room.

BACKGROUND OF THE INVENTION

A C-arm can be used in an operating room in order to obtain X-ray images of a patient during a surgical intervention.

The C-arm comprises between one and six degrees of freedom: up to three degrees of freedom in translation in three orthogonal planes and up to three degrees of freedom in rotation according to three orthogonal axes.

During a surgical intervention, different users may have to actuate the C-arm in order to acquire X-ray images of the patient or to remove the C-arm from the patient when no X-ray acquisition is required.

To that end, the user may have a control panel comprising a plurality of actuation buttons, each button being dedicated to a movement of the C-arm according to a respective degree of freedom. For example, each button may display a pictogram with an arrow representing schematically the direction of the corresponding movement.

Alternatively, the user may have a joystick wherein the stick can be actuated in a plurality of directions, each direction being associated with a movement of the C-arm according to a respective degree of freedom.

However, since the movement of the C-arm is complex (combination of rotation(s) and translation(s)), in some positions of the C-arm the user is not able to select the correct button(s) in view of obtaining the desired movement. This is because even if the buttons each display a pictogram, this representation of the movement is given in a generic way, i.e. relative to a rest position. However, the mental scheme of the user may not be suited to the indication provided on the buttons.

As a result, the user often selects a wrong button and thus may reach the desired position only after a succession of trial-and-error selections, which are time-consuming and potentially generative of collisions with user, patient or furniture.

In addition, the position of the user relative to the C-arm may also vary during the surgical intervention. For example, if the user is the surgeon or his assistant, the user may move from a position from which he sees the C-arm from the left to a position from which he sees the C-arm from the right, and conversely. In some cases, if the user is in a favorable point of view, the selection of the appropriate button will be intuitive, whereas if the user is in a different point of view, the selection of the correct actuation button will not be intuitive.

BRIEF DESCRIPTION OF THE INVENTION

A goal of the invention is thus to provide a more ergonomic and intuitive way of controlling the movement of a C-arm.

An object of the invention is a method for controlling movement of a motorized C-arm, comprising:
receiving position information of a user relative to the C-arm,
continuously receiving current position information of the C-arm relative to a reference position of the C-arm,
from said current position information and from the position information of the user, computing a graphical representation of the current position of the C-arm according to the user's point of view,
from the computed graphical representation of the current position of the C-arm, computing a graphical representation of at least one command button suited to the current position information of the C-arm and to the user's point of view to move the C-arm in a determined direction according to a respective degree of freedom,
displaying on a control panel a graphical user interface comprising said computed representation of the current position of the C-arm and said at least one command button.

According to an embodiment, said method further comprises updating the position information of the user relative to the C-arm and updating the graphical representation of the at least one command button based on said updated position information.

According to an embodiment, when the C-arm is in a stop position for at least one degree of freedom, the command button of the graphical user interface and/or the respective tactile zone is disabled.

According to a preferred embodiment, the command button comprises at least one of: a color, a texture and a pictogram specific to a respective degree of freedom of the C-arm, and wherein said color, texture and/or pictogram is further displayed on the graphical representation of the C-arm.

According to an embodiment, the control panel is embedded in a remote command device intended to be held by a user in the operating room.

According to another embodiment, the control panel is embedded in a computer command station intended to be located in the operating room.

Advantageously, when a user of the remote command device and a user of the computer command station are not on the same side of the C-arm, different graphical user interfaces are displayed on each respective control panel.

According to an embodiment, the position information of the user relative to the C-arm is selected from a limited group of point of views.

More specifically, the position information of the user relative to the C-arm may be given by the user by selecting one point of view among said group.

According to another embodiment, the position information of the user is obtained from position sensors arranged on the user and/or on the control panel and the C-arm.

Another object of the invention is a device for controlling movement of a motorized C-arm, comprising:
a control panel for displaying a graphical user interface comprising a representation of a current position of the C-arm and at least one command button for controlling a movement of the C-arm in a determined direction according to a respective degree of freedom,
a processor capable of communicating with the control panel and configured to carry out the method described above.

According to an embodiment, said control panel is embedded in a remote control device intended to be held by a user in the operating room.

According to another embodiment, said control panel is embedded in a computer command station intended to be located in the operating room.

Another object of the invention is a surgical system comprising a motorized C-arm and a device for controlling movement of said C-arm as described above.

BRIEF DESCRIPTION OF THE DRAWINGS

Further features and advantages of the invention will be apparent from the description to follow, based on the appended drawings wherein.

DETAILED DESCRIPTION OF EMBODIMENTS OF THE INVENTION

Motorized C-Arm

Figure 1:
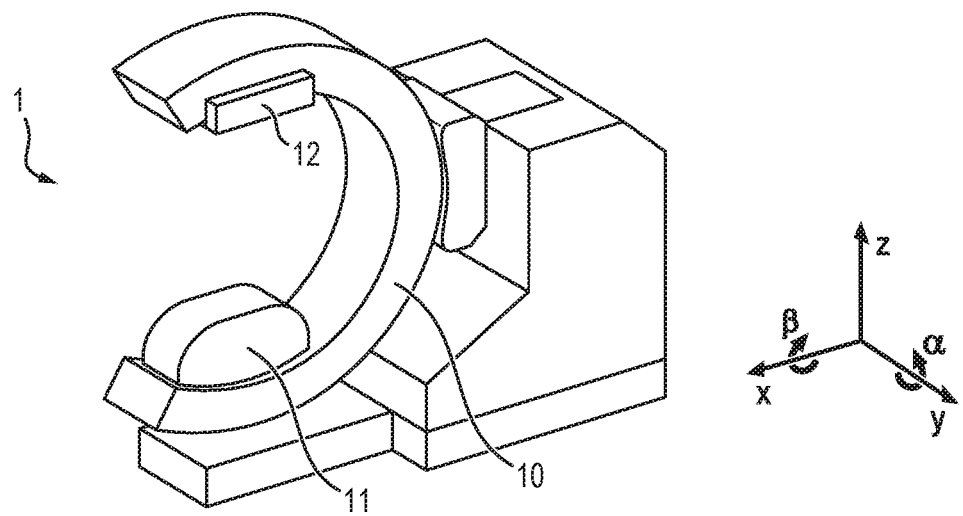
FIG. 1 shows a perspective view of a motorized C-arm in rest position.

FIG. 1 shows a perspective view of a motorized C-arm 1 in rest position.

In a conventional way, the C-arm 1 comprises an arch 10 supporting an X-ray source 11 and an image detector 12 opposite to the X-ray source. Preferably, the arch also comprises an anti-collision equipment which is known per se and thus does not need to be described in detail here.

The arch has a C-shape allowing its arrangement around a table (not shown) on which a patient is lying.

The C-arm comprises up to three degrees of freedom in translation in three orthogonal planes and up to three degrees of freedom in rotation according to three orthogonal axes.

Advantageously, the arch of the C-arm is mounted on a cart (not shown), which is a mobile trolley.

With respect to the table, the arch can be translated horizontally (x-direction, which is perpendicular to the longitudinal axis of the table), laterally (y-direction, which is parallel to the longitudinal axis of the table) or vertically (z-direction).

The arch can further be pivoted with respect to the table in up to three degrees of freedom in rotation, i.e. at least a rotation $\alpha$ around the y-direction, and a rotation $\beta$ around the x-direction.

Each degree of freedom of the C-arm is controlled by a respective motor (not shown).

The position of each motor with respect to a rest position of the C-arm is known, e.g. using a respective encoder.

By "rest position" is meant the position when the arch 10 is in a vertical plane ($\beta=0°$), the X-ray source 11 is below the table in down position ($\alpha=0°$ and the arch is brought horizontally, laterally and vertically in the minimal position (Tx=0, Ty=0, Tz=0).

Surgical System

Figure 2:
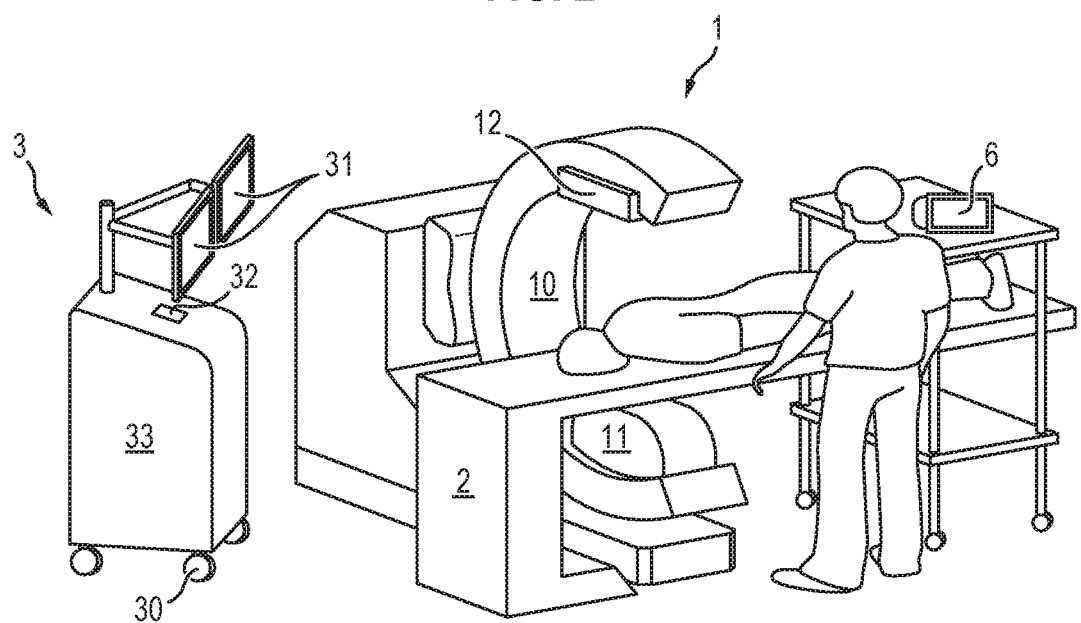
FIG. 2 shows a perspective view of a surgical system including a C-arm.

FIG. 2 shows a perspective view of the surgical system including the above-described C-arm 1.

In addition to the C-arm, the system comprises a table 2 on which a patient is intended to lye and a surgical station 3.

The surgical station 3 comprises a mobile trolley 30 that supports at least one user monitor 31, at least one user interface 32, a computer 33, the image detector processing unit and a power supply.

The station 3 is connected to the C-arm 1 in order to receive the images acquired by the image detector and to control the C-arm. In particular, the computer is configured to control: the trajectory imposed to the arch via order to motor controllers, orders for X-ray emission and image acquisition, display of radiological images displayed on the monitor, patient data management and risk management during the procedure.

The system further comprises at least one control panel intended to be used by a user to actuate the C-arm to reach a desired position and orientation. The control panel may be integrated to the surgical station (such as monitor 31 or user interface 32) or may be physically distinct from the surgical station, e.g. in the form of a handheld device 6 that can be put in any place of the operating room, either in a sterile or non-sterile region.

Control Panel

Figure 3:
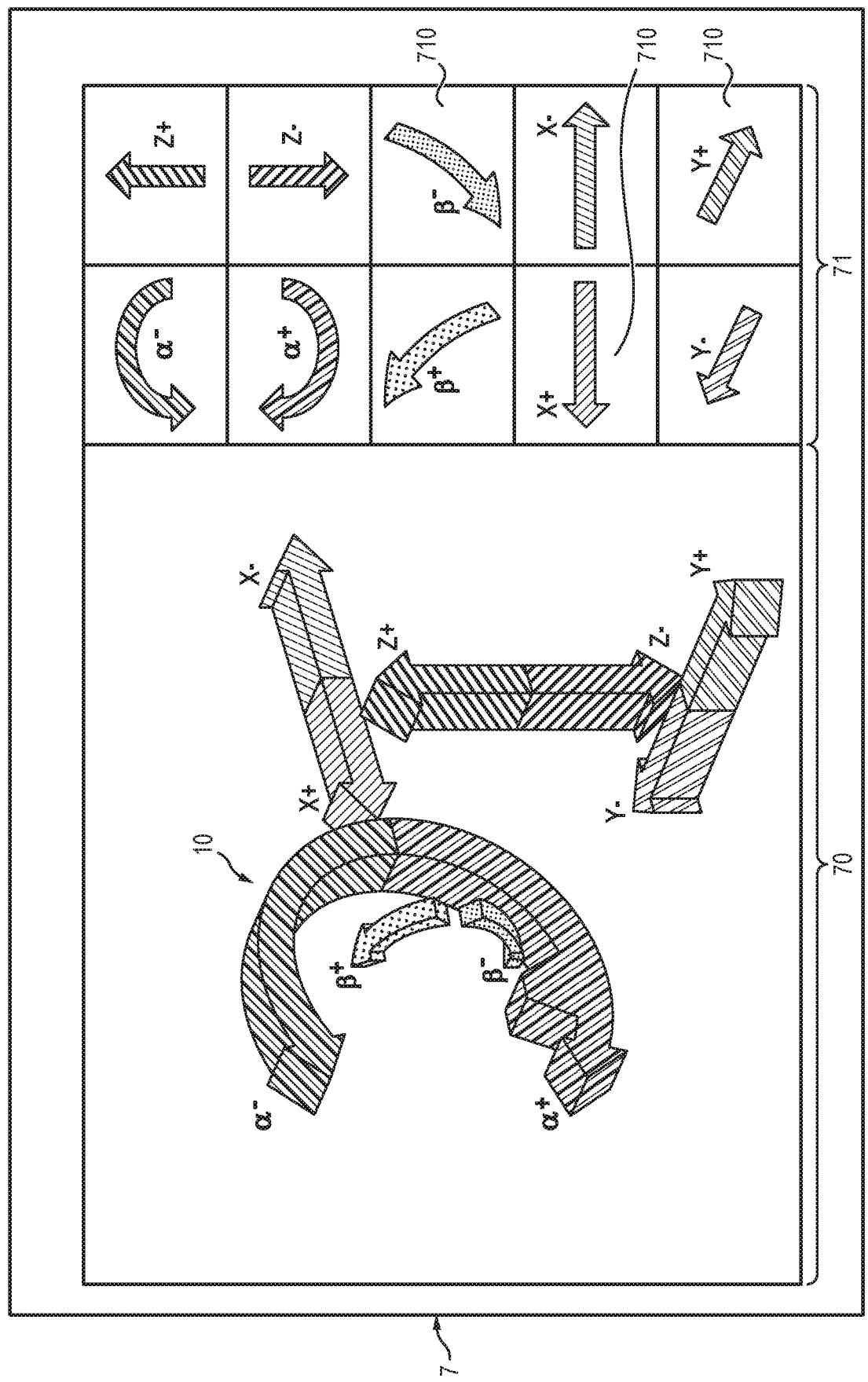
FIGS. 3-4 shows an embodiment of a graphical representation of the C-arm on the control panel in two different positions of the C-arm.

FIG. 3 is an exemplary view of a control panel comprising a graphical user interface 7 according to an embodiment of the invention.

The graphical user interface 7 comprises an area 70 wherein a graphical representation of the current position of the C-arm is represented, along with the directions of actuation of the various degrees of freedom.

For example, the arch is represented as a portion of a circle 10' ended with two arrows showing the directions $\alpha+$, $\alpha-$ of rotation around the y-direction. The three degrees of freedom in translation are represented as opposite arrows showing the directions x+, x− along the x-direction, y+, y− along the y-direction, and z+, z− along the z-direction. The degree of freedom in rotation around the x-direction is represented as curved arrows showing the directions $\beta+$, $\beta-$ of rotation.

Figure 4:
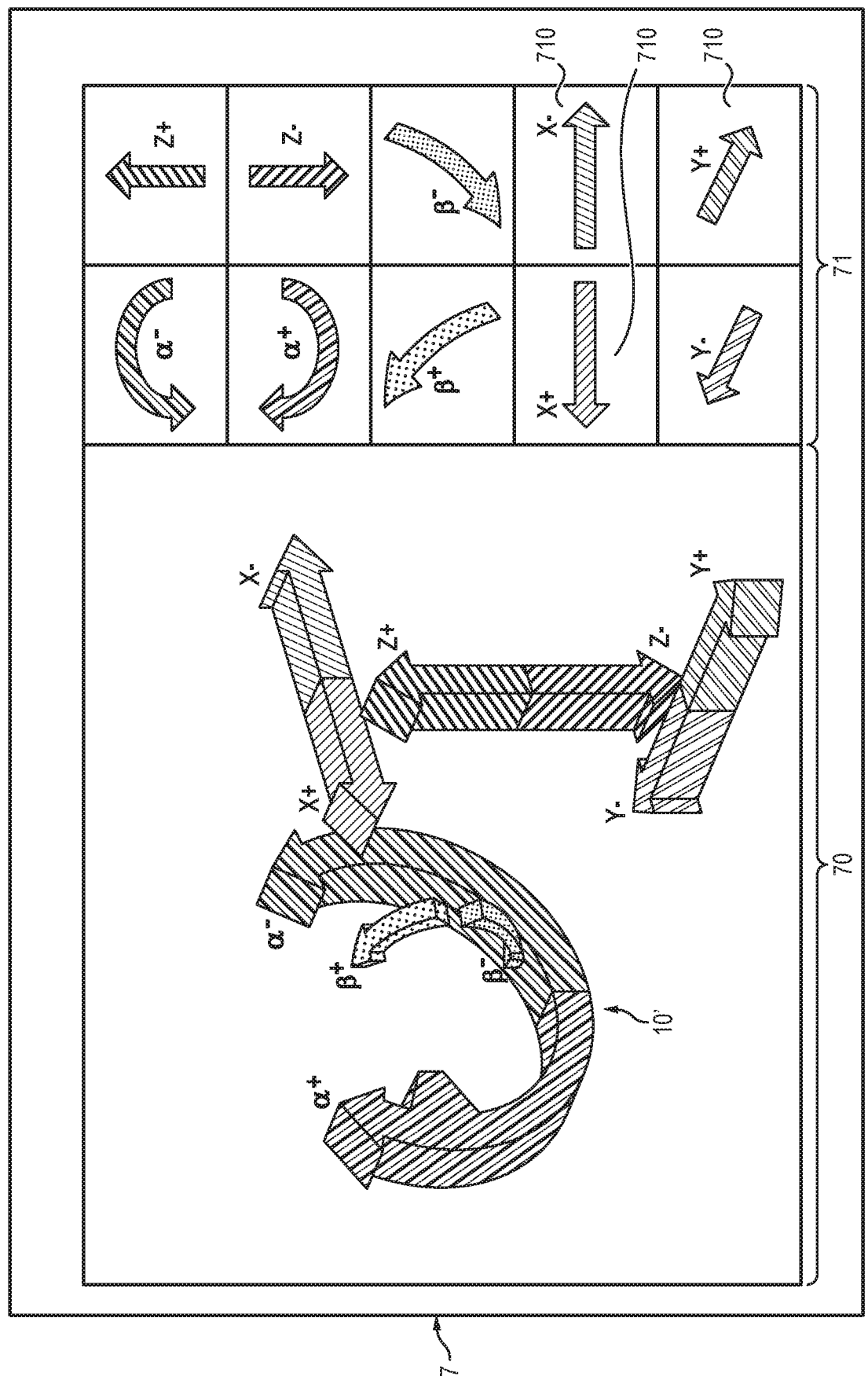

According to an advantageous embodiment, each arrow is represented with a specific color and/or texture in order to be easily distinguishable from the other ones. FIG. 4 is an exemplary view of the control panel of FIG. 3 after rotation of the C-arm around the y-direction. As compared to FIG. 3, the representation 10' of the C-arm has been rotated in accordance with the applied rotation. The other degrees of freedom have not been changed and are thus represented in the same way as in FIG. 3.

Of course, the graphical representations of the C-arm and of the degrees of freedom as shown in FIGS. 3-4 are only illustrative and one could adjust the shape, size, color and/or texture of these elements, for example in order to improve the ergonomics of the system, without departing from the scope of the present invention.

In the embodiment of FIGS. 3-4, the graphical user interface 7 also comprises a tactile area 71 formed of a plurality of independent tactile sub-areas 710. Each sub-area

710 is dedicated to the actuation of the C-arm according to one given direction by causing the respective motor to move the C-arm.

According to an embodiment, each sub-area has the same color and/or texture as the respective arrow on the graphical representation area.

According to a preferred embodiment shown in FIGS. 3-4, a pictogram having an arrow shape is displayed on each tactile sub-area 710 to represent the direction of the degree of freedom controlled by the respective tactile sub-area.

Said pictogram and/or color or texture can also appear onto the C-arm itself, in order to help the user intuitively understand the relationship between the real C-arm and its graphical representation.

The position and/or orientation of the pictogram may advantageously change if the position of the C-arm changes and/or if the position of the user with respect to the C-arm changes. This may improve the ergonomics of the system since this updated representation of the pictogram provides a more intuitive understanding by the user of the movement(s) to be applied to the C-arm in order to bring it to the desired position.

When the user wants to actuate the C-arm along at least one of its degrees of freedom, he applies a finger on the sub-area showing the pictogram corresponding to the desired degree of freedom.

For example, if the user wants to raise the C-arm vertically, he applies a finger onto the sub-area containing the arrow z+.

Figure 5:
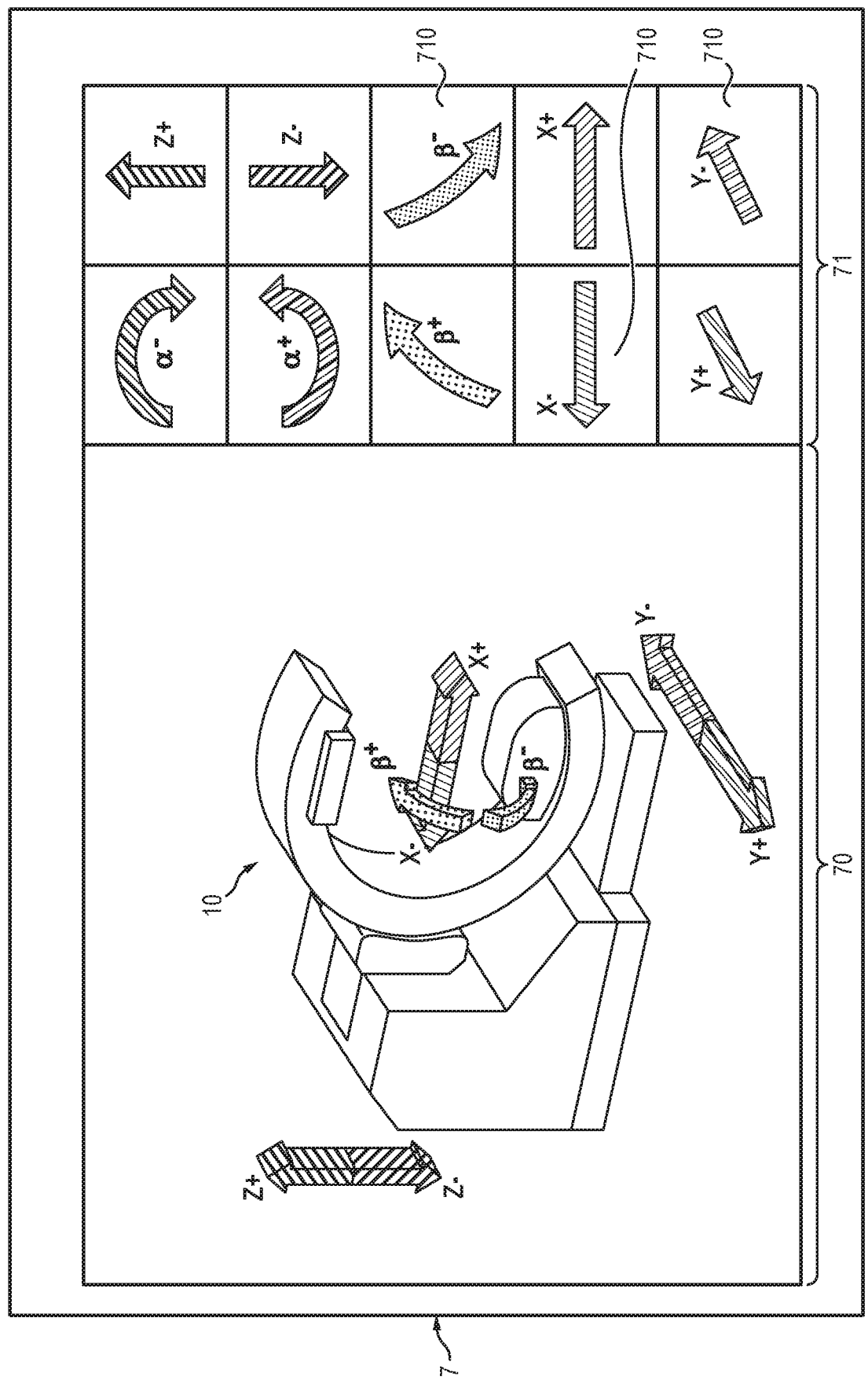
FIG. 5 shows another embodiment of a graphical representation of the C-arm on the control panel.

FIG. 5 shows an alternative representation of the C-arm on the graphical representation area 70 of the control panel 7. In this case, the C-arm is not represented by a mere portion of circle but by a simplified representation of its external shape showing its different components. The degrees of freedom are represented as arrows similar to the ones of FIGS. 3-4.

One can note that the C-arm is not seen from the same point of view in FIGS. 3-4 (the user facing the C-arm with the C-arm on his/her left) as in FIG. 5 (the user facing the C-arm with the C-arm on his/her right). In order to provide a better ergonomics of the system, the pictograms of the tactile sub-areas 710 are represented in an orientation that corresponds to the user's point of view. For example, in the case of FIGS. 3-4, the x+ direction (translation along the x-direction in order to increase the distance of the C-arm from the rest position x=0) is represented by an arrow-shaped pictogram oriented towards the left of the figure in FIGS. 3-4, whereas the same direction of actuation of the C-arm is represented by an arrow-shaped pictogram oriented towards the right in FIG. 5. In addition, it can be noted that the relative positions of the tactile sub-areas for x+ and x− directions are inverted in FIG. 5 as compared to FIGS. 3-4, still in order to optimize the ergonomics of the system.

According to another embodiment (not shown), the control panel may comprise a simple screen to display the representation of the C-arm as explained above and a keyboard comprising LEDS allowing changing the content of each key. See for example the Optimus OLED Keyboard (http://www.legitreviews.com/future-look-the-optimus-organic-led-keyboard_247).

Detection of the User's Position

The user may be the surgeon and/or any person from the medical staff present in the operating room.

As will be explained in further detail below, there may be two users located at different positions in the operating room, each user using a dedicated control panel.

It is not necessary to know precisely the user's position to carry out the present invention. In general, one may consider that it is sufficient to know whether the user is on the left or on the right of the motorized C-arm and/or whether he/she is on the same or opposite side of the table.

In an embodiment, the detection of the user's position can be done by simply entering the information on the control panel. For example, the control panel may comprise a zone allowing selection of either the left-hand or the right-hand position. Such a zone may comprise two buttons or tactile areas corresponding respectively to the left-hand and the right-hand positions. Alternatively, said zone may comprise a switch allowing switching from the left-hand to the right-hand position, and conversely.

In an alternative embodiment, the user may comprise a sensor that allows detecting his/her position with respect to the C-arm. For example, both the control panel and the C-arm may comprise a localization sensor based on radio-frequency identification or magnetic field based indoor localization to identify relative position of the control panel thus user to the C-arm.

Detection of the Current Position of the C-Arm

The position of the C-arm is known at any time by obtaining the position of each motor encoder with respect to the rest position.

The information is sent to continuously to a processor of the computer of the surgical station or of the control panel itself.

Computation of a Graphical Representation of the Position of the C-Arm

According to an embodiment, the control panel is linked (wirelessly or not) to the computer of the surgical station. In such case, the control panel may not comprise any processor and memory and thus only allows displaying the representation of the C-arm and controlling movement of the C-arm thanks to buttons and/or tactile areas as described above, all necessary computation being carried out by the computer of the surgical station.

According to another embodiment, the control panel comprises its own processor and memory to compute the graphical representation of the C-arm and the aspect of the buttons and/or tactile areas. For example, the control panel can be a tablet PC.

The system comprises (e.g. in the computer of the surgical station or in the control panel) a memory wherein a graphical representation of the C-arm at rest is stored.

The system further comprises a processor (e.g. in the computer of the surgical station or in the control panel) capable of implementing an algorithm to determine, based on the information provided by the encoder(s), modifying the rest representation of the C-arm to represent the current position.

Computation of a Graphical Representation of a Command Button

The system comprises a memory (e.g. in the computer of the surgical station or in the control panel) wherein a graphical representation of each command button when the C-arm is at rest is stored.

The system further comprises a processor (e.g. in the computer of the surgical station or in the control panel) capable of implementing an algorithm to determine, based on the information provided by the encoder(s), modifying the rest representation of the command buttons to represent each command button in a position suited to the current position of the C-arm.

Graphical User Interface

The graphical user interface is designed so as to be optimally ergonomic for the user.

To that end, the graphical user interface provides a representation of the C-arm position that (1) corresponds to the user's current point of view (i.e. basically, the C-arm being seen from the right or from the left, and/or facing the user or being on the same side of the table) and (2) corresponds to the current position of the C-arm. In addition, the graphical user interface also provides a representation of the command button(s) that takes into account the current position of the C-arm.

In this way, the selection of the button to be actuated is rendered fully intuitive to the user.

The representation of the current position of the C-arm is not necessarily continuously updated on the graphical user interface. For example, the representation of the C-arm can be updated at a certain frequency that is compatible with the visual comfort of the user, during movement of the C-arm, whereas no update may be made when the C-arm is immobile.

Various situations will now be described with reference to FIGS. 3-13.

Figure 6:
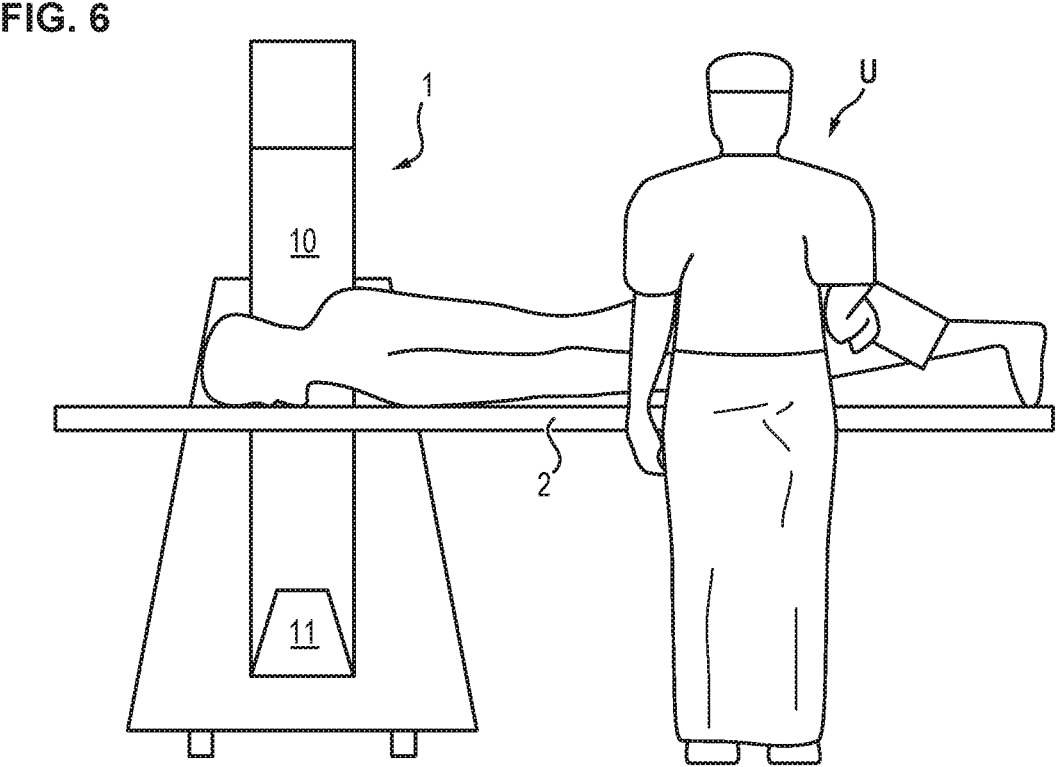
FIG. 6 schematically illustrates the position of a user relative to the C-arm in a first situation.

FIG. 6 illustrates a first situation, wherein the C-arm 1 is in its rest position ($\beta=90°$, $\alpha=0°$) and the user U is in the sterile field, near the table 2, the C-arm facing the user and being on his/her left side.

FIG. 3 is a view of the graphical user interface 7 displaying a graphical representation of the C-arm in its current rest position of FIG. 6 and arrows showing the possible directions of movement of the C-arm along different degrees of freedom. The graphical user interface 7 also comprises several tactile sub-areas 710, each displaying a pictogram corresponding to a respective direction of movement of the C-arm.

Figure 7:
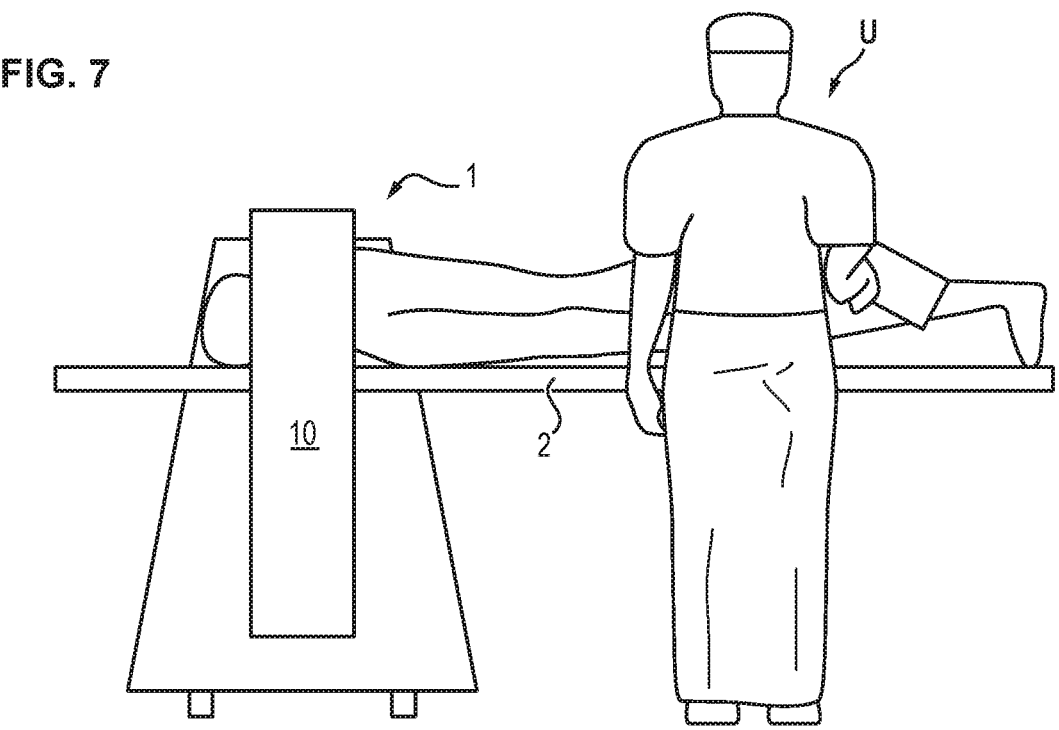
FIG. 7 schematically illustrates the position of a user relative to the C-arm in a second situation.

FIG. 7 illustrates a second situation, wherein the C-arm has moved from the rest position to a lateral position ($\beta=0°$, $\alpha=0°$). As in the situation of FIG. 6, the C-arm 1 faces the user U and is on his/her left side.

FIG. 4 is a view of the graphical user interface displaying the arrows showing the possible movements of the C-arm in its current position of FIG. 7 along the available degrees of freedom.

As compared to FIG. 3, it can be noted that the position and orientation of the representation of the C-arm have been adjusted to correspond to the current position of the C-arm. In this embodiment, the position and orientation of the pictograms in the tactile sub-areas 710 have not changed, since the variation of position of the C-arm were considered as still allowing an intuitive use of the pictograms.

Figure 8:
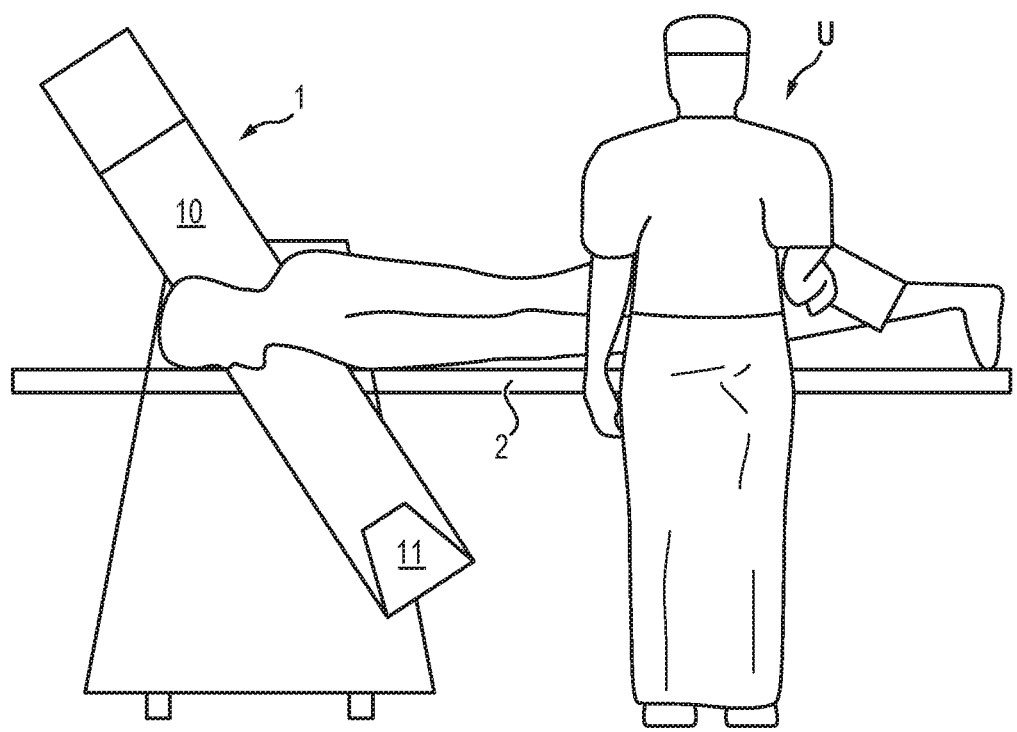
FIG. 8 schematically illustrates the position of a user relative to the C-arm in a third situation.

FIG. 8 illustrates a third situation, wherein the C-arm has moved to another lateral position ($\beta=90°$, $\alpha=40°$). As in the situation of FIGS. 6 and 7, the C-arm 1 faces the user U and is on his/her left side.

Figure 9:
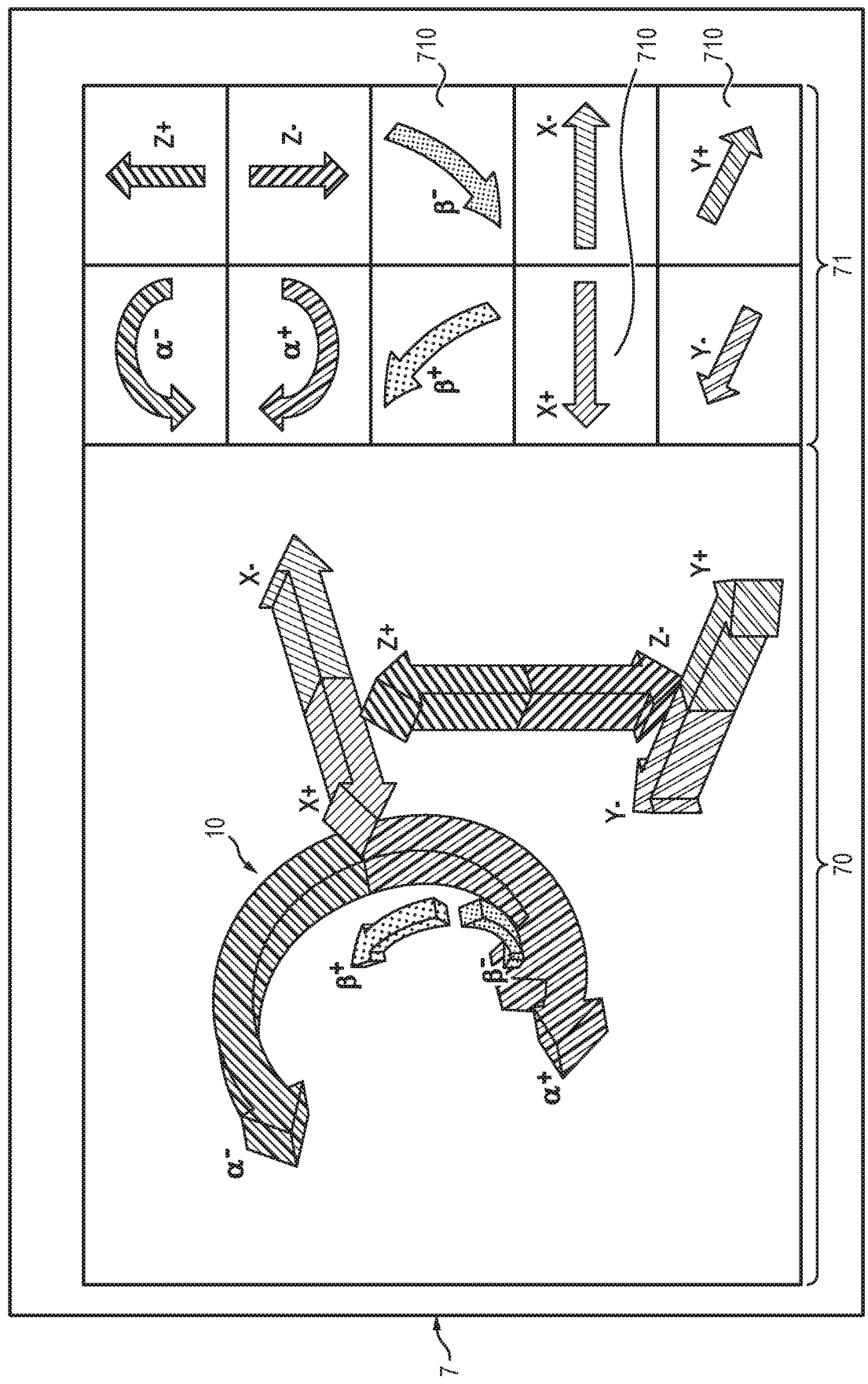
FIG. 9 shows an embodiment of a graphical representation of the C-arm on the control panel configured for a user in the situation of FIG. 8.

FIG. 9 is a view of the graphical user interface displaying a graphical representation of the C-arm showing the possible movements of the C-arm along the available degrees of freedom in its current position of FIG. 8.

As compared to FIGS. 3 and 4, it can be noted that the position and orientation of the representation of the C-arm have been adjusted to correspond to the current position of the C-arm. In this embodiment, the position and orientation of the pictograms in the tactile sub-areas 710 have not changed, since the variation of position of the C-arm were considered as still allowing an intuitive use of the pictograms.

Figure 10:
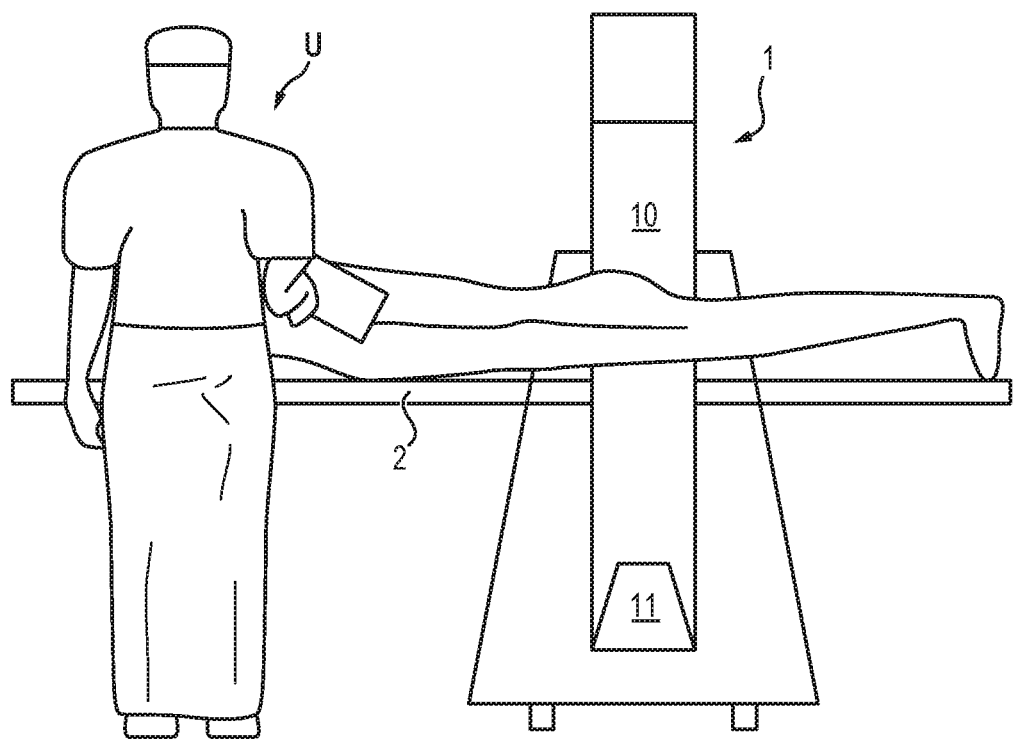
FIG. 10 schematically illustrates the position of a user relative to the C-arm in a fourth situation.

FIG. 10 illustrates a fourth situation, wherein the C-arm 1 is in its rest position ($\beta=90°$, $\alpha=0°$) and the user U is in the sterile field, near the table 2, the C-arm facing the user and being on his/her right side.

Figure 11:
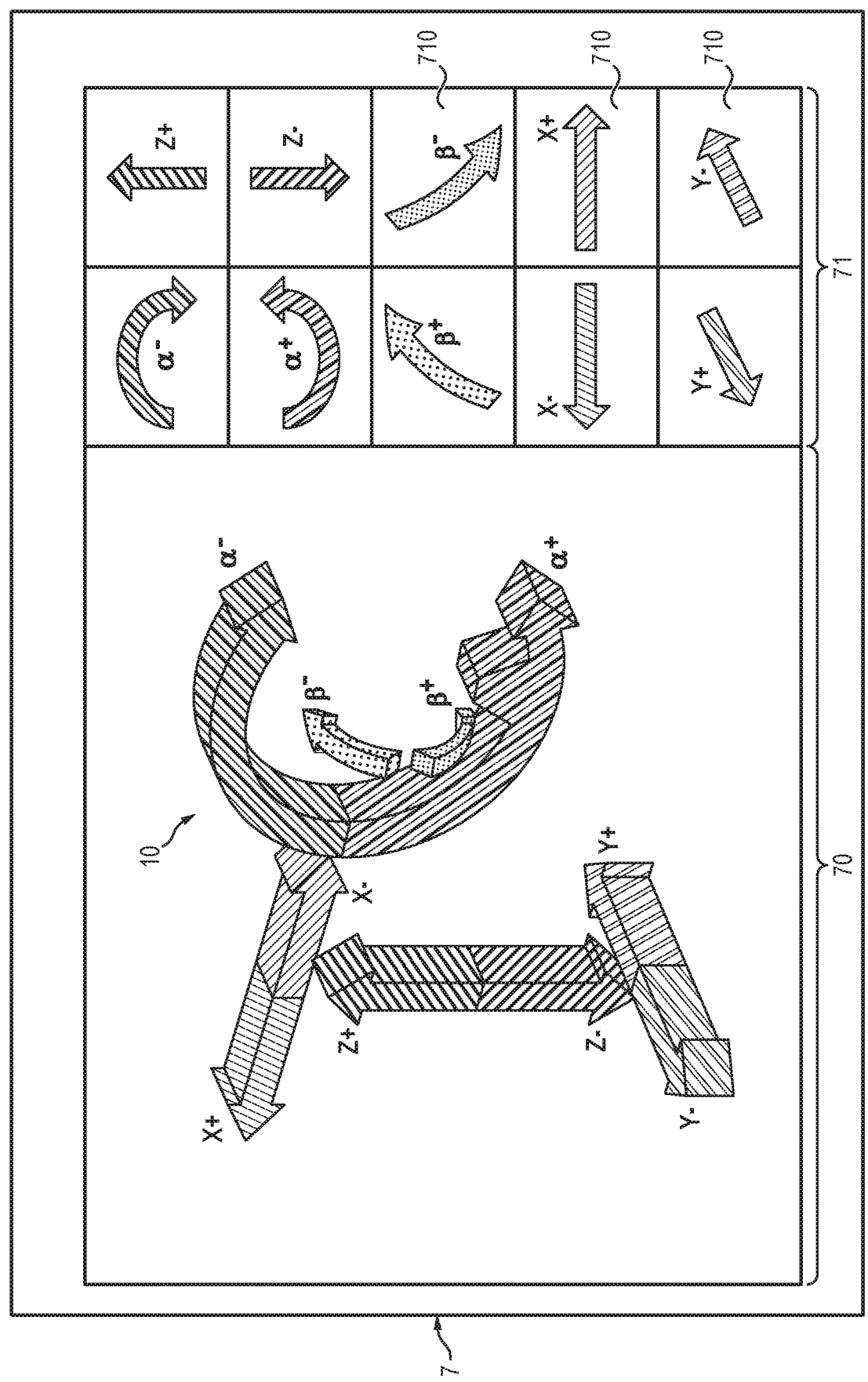
FIG. 11 shows an embodiment of a graphical representation of the C-arm on the control panel configured for a user in the situation of FIG. 10.

FIG. 11 is a view of the graphical user interface displaying a graphical representation of the C-arm in its current rest position of FIG. 10 and the arrows showing the possible movements of the C-arm in its current position of FIG. 10 along the available degrees of freedom.

As compared to FIG. 3, it can be noted that the position and orientation of the representation of the C-arm have been adjusted to correspond to position of the user with respect to the C-arm. In other words, the point of view takes into account the position of the user relative to the C-arm. In addition, the position and orientation of the pictograms in the tactile sub-areas have also been adjusted in order to allow an intuitive use of the pictograms for the user in the corresponding position.

In the case several users have to actuate the C-arm, each user preferably has a dedicated control panel. For example, one user may use a control panel integrated to the surgical station, whereas another user may have a remote control unit such as a handheld device. This allows providing to each user at the same time a graphical representation of the C-arm and the command buttons that is suited to each user's point of view.

Figure 12:
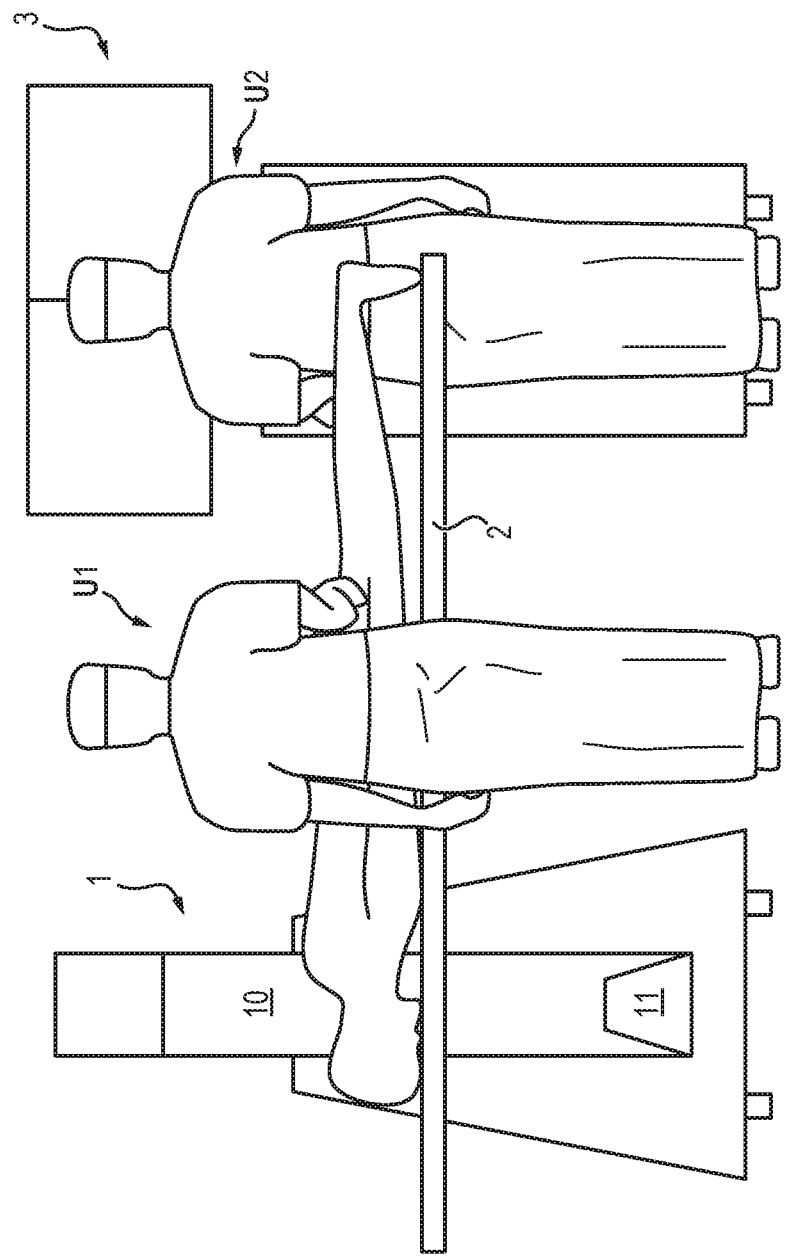
FIGS. 12-13 schematically illustrate the positions of two users relative to the C-arm in fifth and sixth situations.
Figure 13:
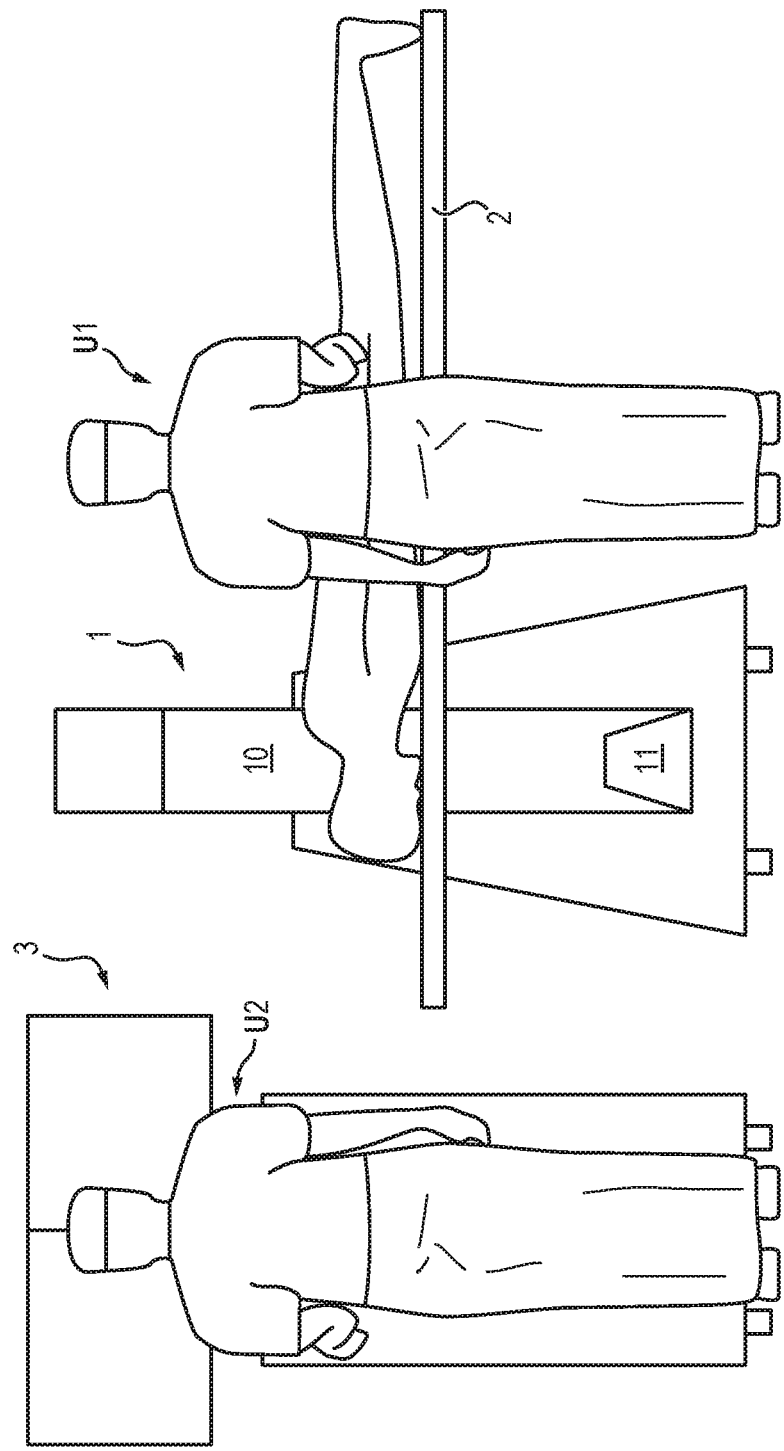

FIG. 12 illustrates another configuration, wherein two users are in the operating room. The C-arm is in the rest position as in FIG. 6. A first user U1 stands in the sterile field, near table 2 facing the C-arm with the C-arm on his/her left, as in FIG. 6. A second user U2 stands in front of the surgical station 3, remote from the sterile field. In the configuration of FIG. 12, the second user 12 has the C-arm on his left. In such case, the graphical representation of the C-arm and the pictograms in the tactile sub-areas of the control panel is the same for both users, and identical to the one illustrated in FIG. 3.

In case the second user is on the left of the C-arm (see FIG. 13), the point of view of both users is different and the control panels dedicated to each user do not display the same information. For user U1, the graphical representation of the C-arm and the pictograms is the same as in FIG. 3. For user U2, the graphical representation of the C-arm and the pictograms is the same as in FIG. 11.

According to an embodiment, a tactile sub-area—or any other command button—may be disabled in case no further movement is possible in the corresponding direction for a given degree of freedom. For example, the pictogram displayed in this sub-area may be shaded in order to show to the user that no action is possible with this sub-area.

The invention claimed is:

1. A method for controlling movement of a motorized C-arm, comprising:
   receiving position information of a user relative to the C-arm,
   continuously receiving current position information of the C-arm relative to a reference position of the C-arm,
   from said current position information and from the position information of the user, computing a graphical representation of the current position of the C-arm according to a user's point of view,
   from the computed graphical representation of the current position of the C-arm, computing a graphical representation of at least one command button suited to the current position information of the C-arm and to the user's point of view to move the C-arm in a determined direction according to a respective degree of freedom, displaying on a control panel a graphical user interface comprising said computed representation of the current position of the C-arm and said at least one command button.

2. The method according to claim 1, further comprising updating the position information of the user relative to the C-arm and updating the graphical representation of the at least one command button based on said updated position information.

3. The method according to claim 1, wherein when the C-arm is in a stop position for at least one degree of freedom, the command button of the graphical user interface and/or the respective tactile zone is disabled.

4. The method according to claim 1, wherein the command button comprises at least one of: a color, a texture and a pictogram specific to a respective degree of freedom of the C-arm, and wherein said color, texture and/or pictogram is further displayed on the graphical representation of the C-arm.

5. The method according to claim 1, wherein the control panel is embedded in a remote command device configured to be held by a user in the operating room.

6. The method according to claim 1, wherein the control panel is embedded in a computer command station configured to be located in the operating room.

7. The method according to claim 1, wherein a first control panel is embedded in a remote command device configured to be held by a user in the operating room and a second control panel is embedded in a computer command station configured to be located in the operating room and wherein when a user of the remote command device and a user of the computer command station are not on the same side of the C-arm, different graphical user interfaces are displayed on each respective first or second control panel.

8. The method according to claim 1, wherein the position information of the user relative to the C-arm is selected from a limited group of point of views.

9. The method according to claim 8, wherein the position information of the user relative to the C-arm is given by the user by selecting one point of view among said group.

10. The method according to claim 1, wherein the position information of the user is obtained from position sensors arranged on the user and/or on the control panel and the C-arm.

11. A device for controlling movement of a motorized C-arm, comprising:
a control panel for displaying a graphical user interface comprising a representation of a current position of the C-arm and at least one command button for controlling a movement of the C-arm in a determined direction according to a respective degree of freedom,
a processor capable of communicating with the control panel and configured to carry out the following steps:
receiving position information of a user relative to the C-arm,
continuously receiving current position information of the C-arm relative to a reference position of the C-arm,
from said current position information and from the position information of the user, computing a graphical representation of the current position of the C-arm according to a user's point of view,
from the computed graphical representation of the current position of the C-arm, computing a graphical representation of at least one command button suited to the current position information of the C-arm and to the user's point of view to move the C-arm in a determined direction according to a respective degree of freedom,
displaying on the control panel a graphical user interface comprising said computed representation of the current position of the C-arm and said at least one command button.

12. The device according to claim 11, wherein said control panel is embedded in a remote control device configured to be held by a user in the operating room.

13. The device according to claim 11, wherein said control panel is embedded in a computer command station configured to be located in the operating room.

14. A surgical system comprising a motorized C-arm and the device according to claim 11.

* * * * *